US012806445B2

(12) United States Patent
Krishnamurthi et al.

(10) Patent No.: US 12,806,445 B2
(45) Date of Patent: Nov. 24, 2026

(54) TARGET STRUCTURE TRACKING BASED ON PHASE-CONTRAST AND/OR DARK-FIELD IMAGE DATA FOR RADIATION THERAPY

(71) Applicant: SIEMENS HEALTHINEERS INTERNATIONAL AG, Steinhausen (CH)

(72) Inventors: Vidhya Krishnamurthi, Los Altos, CA (US); Jörg Freudenberger, Kalchreuth (DE); Thomas Weber, Hausen (DE); Michael Folkerts, Costa Mesa, CA (US)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 137 days.

(21) Appl. No.: 18/809,498

(22) Filed: Aug. 20, 2024

(65) Prior Publication Data

US 2026/0054094 A1 Feb. 26, 2026

(51) Int. Cl.

| | |
|---|---|
| ***A61B 6/00*** | (2024.01) |
| ***A61N 5/10*** | (2006.01) |
| ***G06T 7/246*** | (2017.01) |

(52) U.S. Cl.

CPC ............ *A61N 5/1049* (2013.01); *A61B 6/481* (2013.01); *A61B 6/484* (2013.01); *A61N 5/1067* (2013.01);

(Continued)

(58) Field of Classification Search

CPC .............................. A61N 5/10; A61N 2005/10

See application file for complete search history.

(56) References Cited

U.S. PATENT DOCUMENTS

| | | | | |
|---|---|---|---|---|
| 7,522,698 B2 * | 4/2009 | Popescu | ................. | A61B 6/484 378/19 |
| 7,693,256 B2 * | 4/2010 | Brahme | ................. | A61B 6/022 378/62 |

(Continued)

FOREIGN PATENT DOCUMENTS

| | | | | |
|---|---|---|---|---|
| CN | 111325703 A * | 6/2020 | ............... | G06T 5/50 |
| DE | 102013213244 A1 | 1/2015 | | |

(Continued)

OTHER PUBLICATIONS

F. Pfeiffer et al., "Hard-X-ray dark-field imaging using a grating interferometer", Nature Materials, Jan. 13, 2008, pp. 134-137, vol. 7.

(Continued)

*Primary Examiner* — Thomas R Artman

(74) *Attorney, Agent, or Firm* — SU IP CONSULTING

(57) ABSTRACT

Example methods and systems for target structure tracking are provided. In one example, a computer system may obtain projection image data that is generated using an imaging source to emit an imaging beam towards a patient and a detector to image a target structure within the patient during a treatment phase of radiation therapy. Based on the projection image data, the computer system may generate at least one of (a) phase-contrast image data associated with the target structure and (b) dark-field image data associated with the target structure. The computer system may determine position data associated with the target structure by processing at least one of the following: (a) the phase-contrast image data, (b) the dark-field image data and (c) derived image data that is generated based on the phase-contrast image data or the dark-field image data, thereby tracking the target structure during the treatment phase of the radiation therapy.

17 Claims, 9 Drawing Sheets

(52) U.S. Cl.
CPC ........... *A61N 5/107* (2013.01); *A61N 5/1081* (2013.01); *G06T 7/251* (2017.01); *A61N 2005/1059* (2013.01); *A61N 2005/1061* (2013.01); *G06T 2207/10116* (2013.01); *G06T 2207/20081* (2013.01); *G06T 2207/20084* (2013.01); *G06T 2207/30096* (2013.01)

(56) References Cited

U.S. PATENT DOCUMENTS

| | | | | |
|---|---|---|---|---|
| 9,008,398 | B2 | 4/2015 | Mostafavi et al. | |
| 9,474,914 | B2 * | 10/2016 | Thomson | A61N 5/1037 |
| 12,414,753 | B2 * | 9/2025 | Zhao | A61B 6/4452 |
| 2006/0074292 | A1 * | 4/2006 | Thomson | A61B 6/12 600/411 |
| 2007/0183562 | A1 | 8/2007 | Popescu et al. | |
| 2009/0238334 | A1 * | 9/2009 | Brahme | A61B 6/4092 378/41 |
| 2013/0034208 | A1 * | 2/2013 | Heid | A61N 5/1049 378/91 |
| 2014/0119623 | A1 * | 5/2014 | Mostafavi | G06T 7/0014 382/131 |
| 2021/0244374 | A1 | 8/2021 | Zhao | |
| 2023/0011644 | A1 | 1/2023 | Zhao | |
| 2026/0007382 | A1 * | 1/2026 | Zhao | A61B 6/4452 |
| 2026/0054094 | A1 * | 2/2026 | Krishnamurthi | A61N 5/1071 |
| 2026/0097235 | A1 * | 4/2026 | Krishnamurthi | A61N 5/1037 |

FOREIGN PATENT DOCUMENTS

| | | | |
|---|---|---|---|
| DE | 102007036559 | B4 | 2/2015 |
| DE | 102007029730 | B4 | 6/2017 |
| DE | 102006037282 | B4 | 8/2017 |
| DE | 102016214678 | A1 | 2/2018 |
| WO | 2024160339 | A1 | 8/2024 |

OTHER PUBLICATIONS

Franz Pfeiffer et al., “Phase retrieval and differential phase-contrast imaging with low-brilliance X-ray sources”, Nature Physics, Mar. 26, 2006, pp. 258-261, vol. 2.

T.P. Millard et al., Evaluation of microbubble contrast agents for dynamic imaging with x-ray phase contrast, Scientific Reports, Jul. 20, 2015.

A Velroyen et al., “Microbubbles as a scattering contrast agent for grating-based x-ray dark-field imaging”, Physics in Medicine & Biology, Feb. 1, 2013, vol. 58, pp. 37-46.

Non-Published Commonly Owned U.S. Appl. No. 18/906,177, filed Oct. 4, 2024, 52 pages, Siemens Healthineers International AG.

International Search Report and Written Opinion of the International Searching Authority, International application No. PCT/EP2025/078480, Jan. 2, 2026.

* cited by examiner

300

TARGET STRUCTURE TRACKING BASED ON PHASE-CONTRAST AND/OR DARK-FIELD IMAGE DATA FOR RADIATION THERAPY

BACKGROUND

Radiation therapy is a widely used cancer treatment modality that uses high-energy radiation to reduce or eliminate cancerous tumors. In practice, applied radiation does not inherently discriminate between a tumor and proximal healthy structures, such as organs, healthy tissues, etc. Ideally, the objective is to deliver a lethal or curative radiation dose to the tumor, while maintaining an acceptable dose level in the proximal healthy structures. During treatment time, delivery of planned radiation dose may be hindered by the presence of patient motion. In this case, motion management may be performed by tracking the position of a moving target structure and acting upon any deviation from a planned position. In practice, motion management during radiation therapy remains an open problem. In some cases, conventional motion management techniques may contribute to large target margins, limiting the ability of clinicians to spare the healthy tissue surrounding the target structure. Regardless of the strategy used to adapt delivered radiation fields to match or otherwise manage motion of the target structure, the quality, latency, and/or information content within acquired real-time image data still needs improvement to reduce target margins.

SUMMARY

Figure 1:
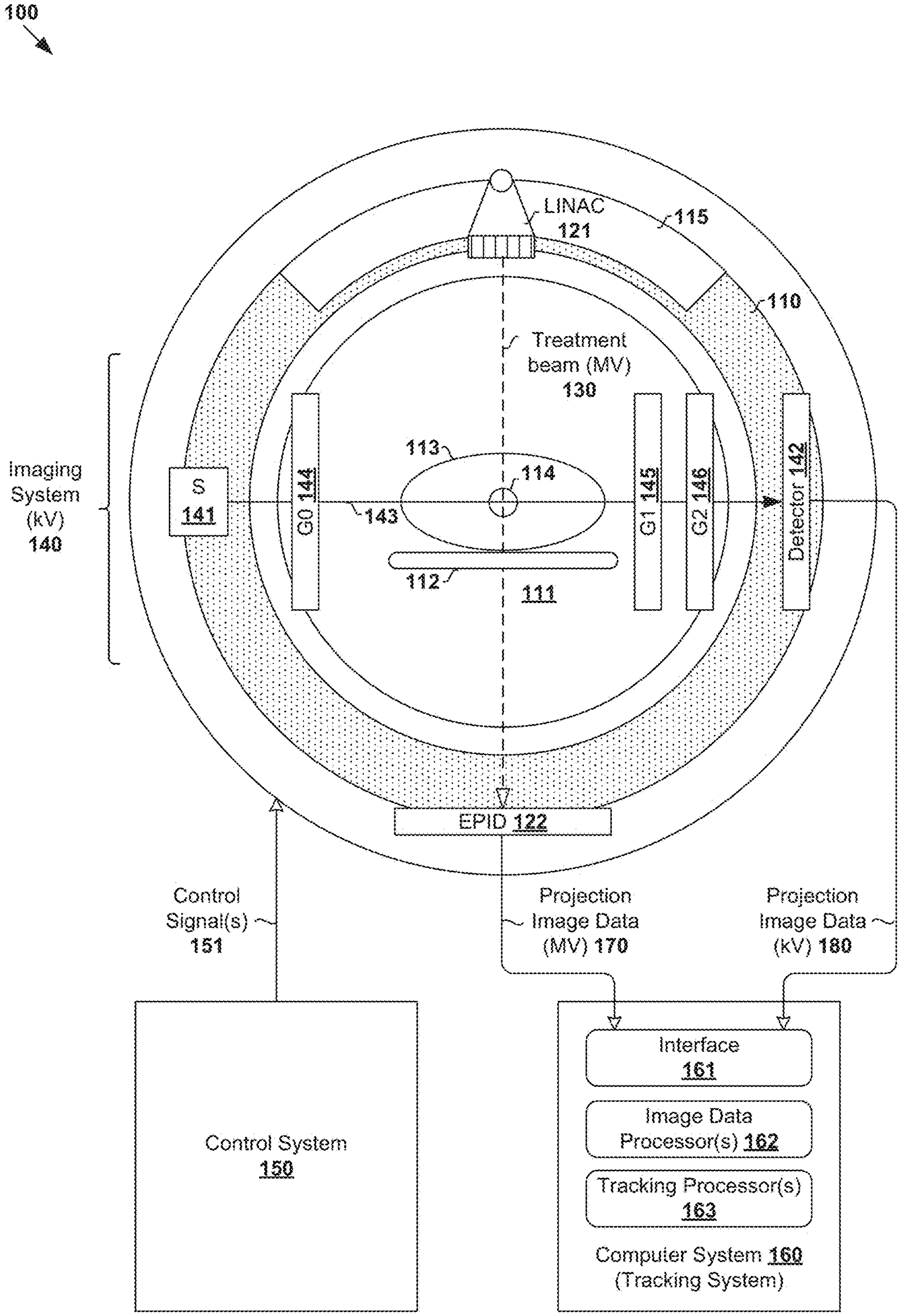
FIG. 1 is a schematic diagram illustrating an example radiation therapy system that includes a grating-based imaging system capable of performing phase-contrast and/or dark-field imaging for target structure tracking.

According to examples of the present disclosure, phase-contrast and/or dark-field imaging may be implemented during a treatment phase of radiation therapy to facilitate target structure tracking. As used herein, the term “target structure tracking” may refer generally to estimating position data associated with a target structure, such as to facilitate motion management, position monitoring and/or verification, target localization or the like during radiation treatment. The term “target structure” may refer generally to any suitable structure that requires tracking, such as tumor, organ-at-risk (OAR), healthy tissue, bony structure (e.g., vertebra), implanted marker, brachytherapy applicator for brachytherapy, etc.

According to a first aspect, examples of the present disclosure provide method(s) and computer system(s) for target structure tracking. In one example, a computer system (see 160 in FIG. 1) may obtain projection image data that is generated using an imaging source to emit an imaging beam towards a patient and a detector to image a target structure within the patient during a treatment phase of radiation therapy. Based on the projection image data, the computer system may generate at least one of (a) phase-contrast image data associated with the target structure and (b) dark-field image data associated with the target structure. The computer system may determine position data associated with the target structure by processing at least one of the following: (a) the phase-contrast image data, (b) the dark-field image data and (c) derived image data that is generated based on the phase-contrast image data or the dark-field image data, thereby tracking the target structure during the treatment phase of the radiation therapy. See also 310-340 in FIG. 3.

According to a second aspect, examples of the present disclosure provide radiation therapy system(s) for target structure tracking. In one example, a radiation therapy system (see 100 in FIG. 1) may include a grating-based imaging system and a computer system for target structure tracking. The grating-based imaging system (see 140 in FIGS. 1-2) may include an imaging source, a detector and multiple gratings that are positioned between the imaging source and the detector. The computer system (see 160 in FIG. 1) may obtain, from the grating-based imaging system, projection image data that is generated using the imaging source to emit an imaging beam towards the multiple gratings and the detector to image a target structure within the patient during a treatment phase of radiation therapy. Based on the projection image data, the computer system may generate at least one of (a) phase-contrast image data associated with the target structure and (b) dark-field image data associated with the target structure. The computer system may determine position data associated with the target structure by processing at least one of the following: (a) the phase-contrast image data, (b) the dark-field image data and (c) derived image data that is generated based on the phase-contrast image data or the dark-field image data, thereby tracking the target structure during the treatment phase of the radiation therapy.

Using examples of the present disclosure, phase-contrast image data and/or dark-field image data may be generated to provide additional information associated with a target structure compared to absorption image data, such as improved soft tissue contrast, better target visibility, etc. The additional information may be used during a treatment phase of radiation therapy to improve the accuracy of target structure tracking. In practice, examples of the present disclosure may be implemented to improve motion management, dose accuracy and conformity and sparing of healthy tissue during a treatment phase of radiation therapy. Examples of the present disclosure should be contrasted against conventional approaches that rely on conventional X-ray imaging that only generates absorption image data for target structure tracking. Examples of the present disclosure should also be contrasted against conventional approaches that use phase-contrast and/or dark-field imaging for diagnostic purposes (i.e., prior to treatment) instead of target structure tracking during radiation therapy treatment.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated herein. Although the terms "first" and "second" are used to describe various elements, these elements should not be limited by these terms. These terms are used to distinguish one element from another. For example, a first element may be referred to as a second element, and vice versa. Independent of the grammatical term usage, individuals with male, female or other gender identities are included within the term.

Radiation Therapy System

FIG. 1 is a schematic diagram illustrating example radiation therapy system 100 that includes grating-based imaging system 140 capable of performing phase-contrast and/or dark-field imaging for target structure tracking. In this example, radiation therapy system 100 has a ring-based configuration that includes a circular gantry. In practice, any alternative configuration may be implemented, such as a C-arm configuration (not shown) that includes a C-shaped gantry, etc. Radiation therapy system 100 may be configured to facilitate kilovolt (kV) imaging using kV imaging beam (see 143) during application of a megavolt (MV) treatment beam (see 130). Projection image data (see 180) obtained using kV imaging may be subsequently processed to generate phase-contrast and/or dark-field image data for target structure tracking according to examples of the present disclosure.

In the example in FIG. 1, radiation therapy system 100 may include gantry 110 having opening 111, patient support or treatment couch 112 for supporting patient 113, control system 150 for controlling operation(s) of gantry 110 using drive system 115 and computer system 160 for, inter alia, target structure tracking according to examples of the present disclosure. During operation of radiation therapy system 100, gantry 110 may rotate about bore or opening 111 when actuated by drive system 115. To facilitate treatment delivery, radiation therapy system 100 may include a radiation source in the form of linear accelerator (LINAC) 121 as well as an imager/detector in the form of MV electronic portal imaging device (EPID) 122. LINAC 121 may generate and direct MV treatment beam 130 towards isocenter 114 through a planning target volume (PTV) while gantry 110 rotates through a treatment arc. In practice, MV treatment beam 130 may be within a high-energy range, such as 1 mega-electron volts (MV) or greater.

Radiation therapy system 100 may be coupled with any suitable computer system(s) to facilitate treatment delivery and imaging, such as control system 150 to control and computer system 160 for target structure tracking. Control system 150 may be configured to generate and send control signal(s) to control the operations of various elements of radiation therapy system 100, such as gantry 110, LINAC 121 and imaging source 141. Computer system 160 may be configured to obtain and process projection imaging data (see 170-180) from EPID 122 and detector 142. Projection image data 180 from grating-based imaging system 140 may be used to facilitate target structure tracking according to examples of the present disclosure.

In practice, computer system 160 may be located in the same physical location as radiation therapy system 100, or in a different location. In both cases, computer system 160 may be communicatively coupled with radiation therapy system 100 via any suitable communication network(s). Computer system 160 may be implemented using one or more physical machines (bare metal machines) and/or virtual machines deployed in a cloud-based environment. Control system 150 and computer system 160 may include any display device(s) and user input device(s), which are not shown for simplicity.

Grating-Based Imaging System

Radiation therapy system 100 may further include on-board kV imaging system 140 to facilitate target structure tracking during radiation therapy using any suitable treatment technique(s). One example treatment technique may be volumetric modulated arc therapy (VMAT), where gantry 110 is rotated around patient 113 during radiation therapy. Another example treatment technique may be static intensity modulated radiotherapy treatment (IMRT) that is delivered with multi-leaf collimator (MLC). Imaging system 140 may include kV imaging source 141 and kV detector 142 (also known as an imaging panel or imager).

Figure 2:
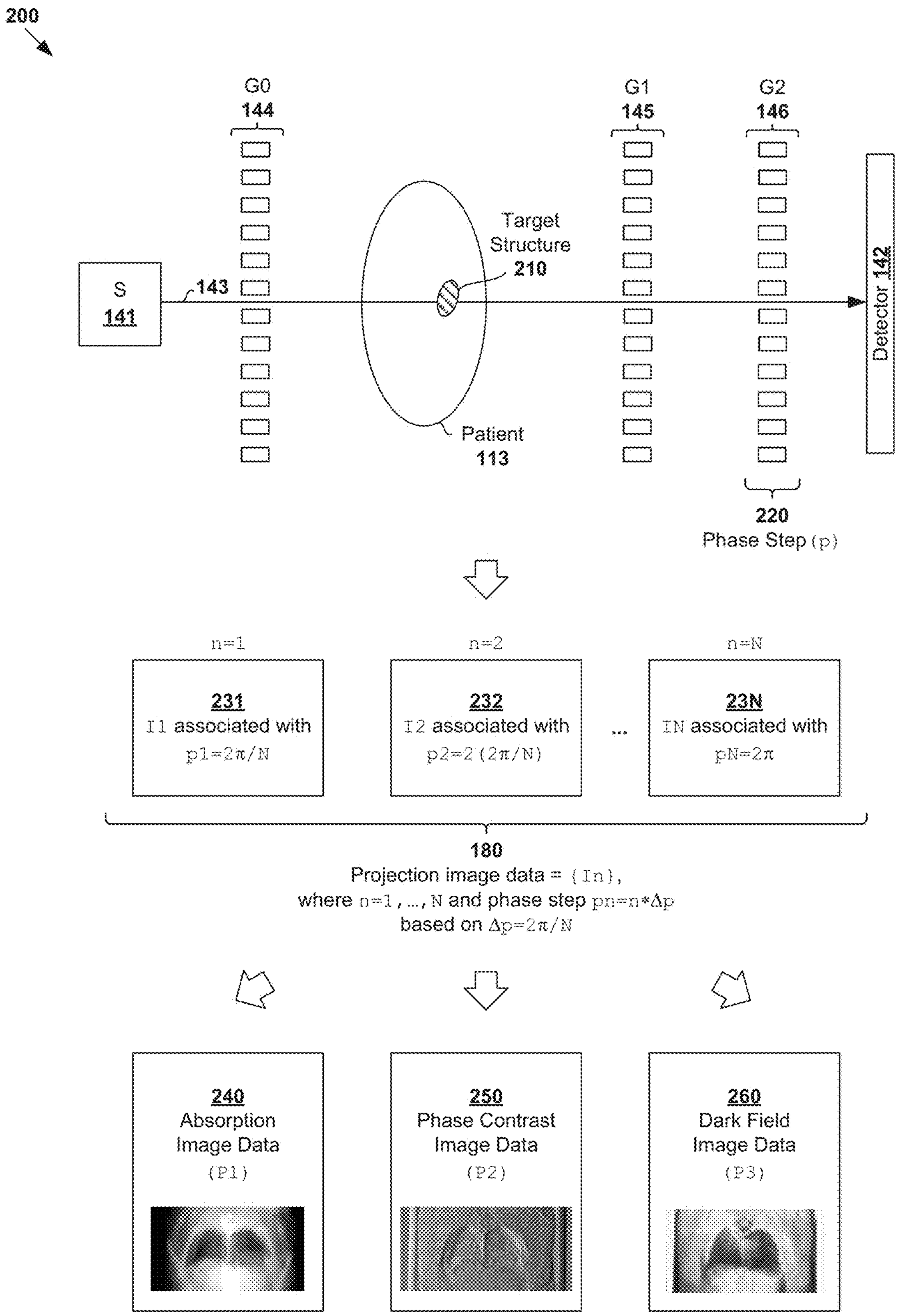
FIG. 2 is a schematic diagram illustrating a detailed example configuration of the grating-based imaging system shown in FIG. 1.

According to examples of the present disclosure, on-board kV imaging system 140 may be a grating-based imaging system that is capable of performing phase-contrast and/or dark-field imaging. A more detailed view is shown in FIG. 2, which is a schematic diagram illustrating detailed example configuration 200 of grating-based imaging system 140 shown in FIG. 1. In practice, X-ray phase-contrast and dark-field imaging may be performed with low-brilliance medical X-ray sources using Talbot-Lau interferometry. A description of Talbot-Lau interferometry may be found in F. Pfeiffer, T. Weitkamp, O. Bunk, and C. David, "Phase retrieval and differential phase-contrast imaging with low brilliance x-ray sources," Nature Phys. 2, 258-261 (2006), which is incorporated herein by reference.

In the example in FIGS. 1-2, grating-based imaging system 140 may include imaging source 141 (labelled "S"), detector 142 and multiple gratings (labelled "G0" to "G2") that are interposed between them. In the case of three gratings, for example, first grating=source grating (G0) 144, second grating=phase grating (G1) 145 and third grating=analyzer grating (G2) 146 may be positioned between source 141 and detector 142. Depending on the exact properties of source 141 and detector 142, gratings 144-146 may have periods in the order of 2 to 50 micrometers (i.e., micrometer-scale gratings).

As used herein, the term "grating" may refer generally to an optical component or structure that includes a number of (e.g., evenly spaced) parallel lines or slits. These parallel lines or slits may diffract X-rays or light, creating interference patterns that may be used to enhance image contrast, such as for materials that are weakly absorbing and would otherwise show low contrast in traditional absorption-based imaging. The term "grating-based imaging system" may refer generally to an imaging system that is capable of performing phase-contrast and/or dark-field imaging, and includes at least an imaging source, a detector and multiple gratings. In practice, any suitable number of gratings (e.g., at least two) may be configured.

Grating-based imaging system 140 may be mounted orthogonally to LINAC 121 while sharing the same isocenter 114. Compared to LINAC 121, kV imaging source 141 may be capable of producing imaging or diagnostic energy in the range of kV, such as below 160 kV, etc. In response to detecting imaging X-ray beams 143 generated by imaging source 141, detector 142 (e.g., pixelated detector, flat-panel imager) may generate suitable projection image data 180. Both imaging source 141 and detector 142 may be moved laterally and longitudinally relative to treatment beam 130, and rotatable around patient 113 on treatment couch 112. The movement of imaging source 141 and detector 142 may be controlled using control system 150. Depending on the desired implementation, imaging system 140 may include a variety of X-ray energies (e.g., single energy or dual energy) and/or gratings to maximize or improve target visibility.

Although one pair of imaging source 141 and detector 142 is shown in FIGS. 1-2, imaging system 140 may include multiple sources and/or detectors, such as to facilitate stereoscopic imaging, etc.

In practice, imaging source 141 may be a medical X-ray source to produce non-coherent, polychromatic X-rays 143. G0 144 may be positioned downstream of the direction of wave propagation to ensure spatial coherence by introducing multiple virtual slit sources. Wavefronts originating from the slit sources of G0 144 may impinge on target structure(s) 210 within patient 113, who is positioned between the G0 144 and G1 145. The wavefronts may be deformed by patient 113 depending on their material properties. Further towards detector 142, G1 145 may be deployed as a phase mask to imprint a periodic phase shift on the wavefronts emitted from G0 144. The resulting intensity pattern from G1 145 may be sampled by a measurement of intensity for a number of grating positions (p) of G2 146. Each grating position p is known as a phase step. The process of adjusting or shifting the phase step may be referred to as phase stepping. Depending on the desired implementation, phase stepping may be performed using active or passive methods. See 220 in FIG. 2.

In the example in FIG. 2, projection image data 180 that is acquired using grating-based imaging system 140 may include a set of multiple (N) projection images denoted as {¿} where n=1, . . . , N. Here, {¿} may be acquired sequentially using detector 142 with patient 113 interposed between G0 144 and G1 145. Note that the measurements may also be done continuously or passively by exploiting intrinsic vibrations of the setup or system. After each projection image (¿) is acquired, the grating position (p) of G2 146 may be moved by, for example, 2π/N of one period. In this case, the $n^{th}$ projection image may be associated with a particular grating position pn, where n=1, . . . , N. For example, p1=¿2π/N for n=1, p2=¿2(2π/N) for n=2, and so on until pN=¿N (2π/N)=¿2π for n=N. See 231-23N in FIG. 2.

Based on projection image data 180, multiple types of image data may be generated or extracted to provide complementary contrasts, such as absorption image data 240 (denoted as P1), phase-contrast image data 250 (denoted as P2) and dark-field image data 260 (denoted as P3). Detailed examples for generating P1 240, P2 250 and P3 260 will be explained using FIGS. 4-5.

As used herein, the term "phase-contrast image data" (also known as "differential phase image data") may refer generally to image data that is generated based on a refraction property of imaging beam(s), such as phase shift(s) caused by the refraction. For example, when an X-ray wave passes through a particular material, it may bend slightly due to its interactions with the material's electron. This bending, which is called refraction, causes a shift in the phase of the X-ray wave. The phase shift may be detected to generate phase-contrast image data, which provides enhanced contrast information. This should be contrasted against standard X-ray imaging, which relies on how much the X-ray intensity varies as it passes through the material.

The term "dark-field image data" may refer generally to image data that is generated based on a scattering property of imaging beam(s). For example, a small-angle or ultra-small-angle scattering signal may be more sensitive to structural variations and/or density variations. Denser materials generally absorb more X-rays, leading to darker areas on the resulting image data. In practice, dark-field image data may provide a better visualization of fine structural details that may not be visible in absorption image data, thereby improving target visibility. The term "absorption image data" (also known as "transmission image data") may refer generally to image data that is generated based on attenuation of imaging beam(s). In general, absorption-based X-ray imaging may rely on the differential absorption of X-rays by different materials.

Target Structure Tracking

According to examples of the present disclosure, target structure tracking may be performed with improved accuracy based on phase-contrast and/or dark-field image data, such as to improve target visibility and soft tissue contrast. In practice, improved accuracy of target structure tracking may in turn reduce the probability of target miss and/or the probability of healthy tissue damage during treatment delivery.

Examples of the present disclosure may be implemented as part of any suitable software suite for target structure tracking and motion management during a treatment phase of radiation therapy.

Figure 3:
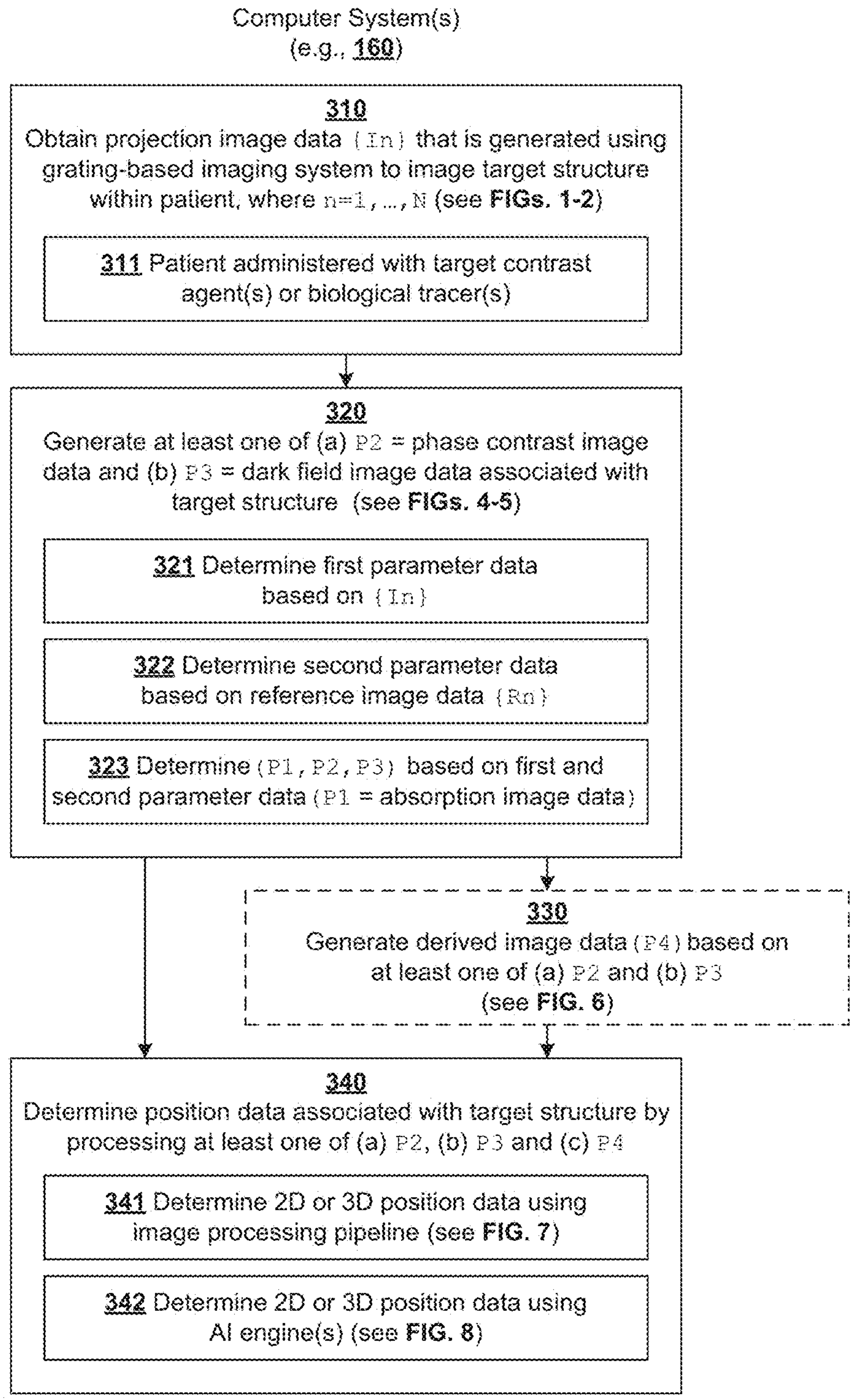
FIG. 3 is a schematic diagram illustrating an example process for a computer system to perform target structure tracking based on phase-contrast and/or dark-field image data for radiation therapy.

In more detail, FIG. 3 is a flowchart illustrating example process 300 for computer system 160 to perform target structure tracking based on phase-contrast and/or dark-field image data for radiation therapy. Example process 300 may include one or more operations, functions, or actions illustrated by one or more blocks, such as 310 to 340. Depending on the desired implementation, various blocks may be combined into fewer blocks, divided into additional blocks, and/or eliminated. Using the example in FIG. 1, example process 300 be performed using computer system 160 capable of acting as a target structure tracking system. Computer system 160 may include any suitable module(s) or component(s) such as interface 161 to interface with radiation therapy system 100 to perform block 310, image data processor(s) 162 to perform blocks 320-330, tracking processor(s) 163 to perform block 340, etc.

At 310 in FIG. 3, computer system 160 may obtain projection image data 180, which may be generated using grating-based imaging system 140 that includes imaging source 141, multiple gratings 144-146 and detector 142. Imaging source 141 may be configured to emit imaging beam(s) 143 towards multiple gratings 144-146 and detector 142 to image target structure(s) 210 within patient 113 during a treatment phase of radiation therapy.

At 320 in FIG. 3, based on projection image data 180, computer system 160 may generate at least one of (a) phase-contrast image data (P2) 250 associated with target structure 210 and (b) dark-field image data (P3) 260 associated with target structure 210. Depending on the desired implementation, block 320 may be performed based on projection image data 180 and reference image data, which is generated using grating-based imaging system 140 without patient 113 (i.e., no subject).

As will be discussed using FIGS. 4-5, block 320 may include determining first parameter data associated with projection image data 180 (see 321) and determining second parameter data associated with the reference image data (see 322). Based on the first parameter data and the second parameter data, various types of image data may be generated (see 323), such as P1 240, P2 250, P3 260 or any combination thereof. The first and second parameter data may be extracted from phase-stepping curves and include intensity offset data, intensity amplitude data, differential phase data (also known as phase shift data), visibility data, etc.

At 330 in FIG. 3, computer system 160 may generate derived image data (denoted as P4) based on at least one of (a) P2 250 associated with target structure 210 and (b) P3 260 associated with target structure 210. Depending on the desired implementation, block 330 may involve applying any suitable function(s) to combine or calculate a ratio between at least two P1 240, P2 250 and P3 260. Some examples will be discussed below using FIG. 6.

At 340 in FIG. 3, computer system 160 may determine position data associated with target structure 210 by processing at least one of the following: (a) P2 250, (b) P3 260 and (c) derived image data (P4), thereby tracking the target structure during a treatment phase of the radiation therapy. In practice, the position data may be two-dimensional (2D) or three-dimensional (3D) position data associated with target structure 210. To determine the position data, computer system 160 may process at least one of P2 250, P3 260 or P4 using an image processing pipeline that includes a motion model (see FIG. 7), artificial intelligence (AI) engine or engines (see FIG. 8), etc.

Examples of the present disclosure may be implemented to take advantage of additional data provided by P2 250 and/or P3 260. In particular, P2 250 and P3 260 may employ fundamentally different physical properties of target structure 210, such as phase shift (i.e., real part of the refractive index) and small angle scattering that depend on a porosity characteristic of target structure 210. In the case of lung cancer treatment, lung tumors are known to be solid compared to surrounding lung tissue that is porous due to the alveoli. This usually results in a large signal difference between a tumor and healthy tissue in P3 260, where border(s) of the tumor may be more easily located during target structure tracking. Further, P2 250 is generally differential in nature in a grating-based phase-contrast imaging setup and expected to have strong signals at the border(s) of a solid structure.

Depending on the desired implementation, patient 113 may be administered with targeted contrast agents or biological tracers to enhance target visibility and improve the detectability of specific cells or cell clusters (see 311 in FIG. 3). Example biological tracers include microbubbles (i.e., ultrasound contrast agents), nanoparticles, peptides, etc. Such biological tracers may selectively bind to any specific cancer cells or healthy tissues to increase phase-contrast and/or dark-field properties. For example, microbubbles may each include a gas core that is surrounded by a surfactant or polymer shell, whose surface may be functionalized with a range of targets. Gold nanoparticles or microparticles may be loaded on tracers to create a more porous structure in or around a target tissue. Any suitable approach may be used to administer the biological tracers, such as intravenous injection, direct injection, oral ingestion, etc.

Example Image Data Generation

Blocks 310-320 will be explained further using FIG. 4, which is a flowchart illustrating example process 400 for computer system 160 to generate absorption image data 240, phase-contrast image data 250 and dark-field image data 260. Example process 400 may include one or more operations, functions, or actions illustrated by one or more blocks, such as 410 to 460. Depending on the desired implementation, various blocks may be combined into fewer blocks, divided into additional blocks, and/or eliminated. The example in FIG. 4 may be implemented using any suitable components of computer system 160, such as interface 161 to interface with detector 142 and processor(s) 162 to generate phase-contrast and/or dark-field image data.

(a) Projection Image Data (With Patient)

Figure 4:
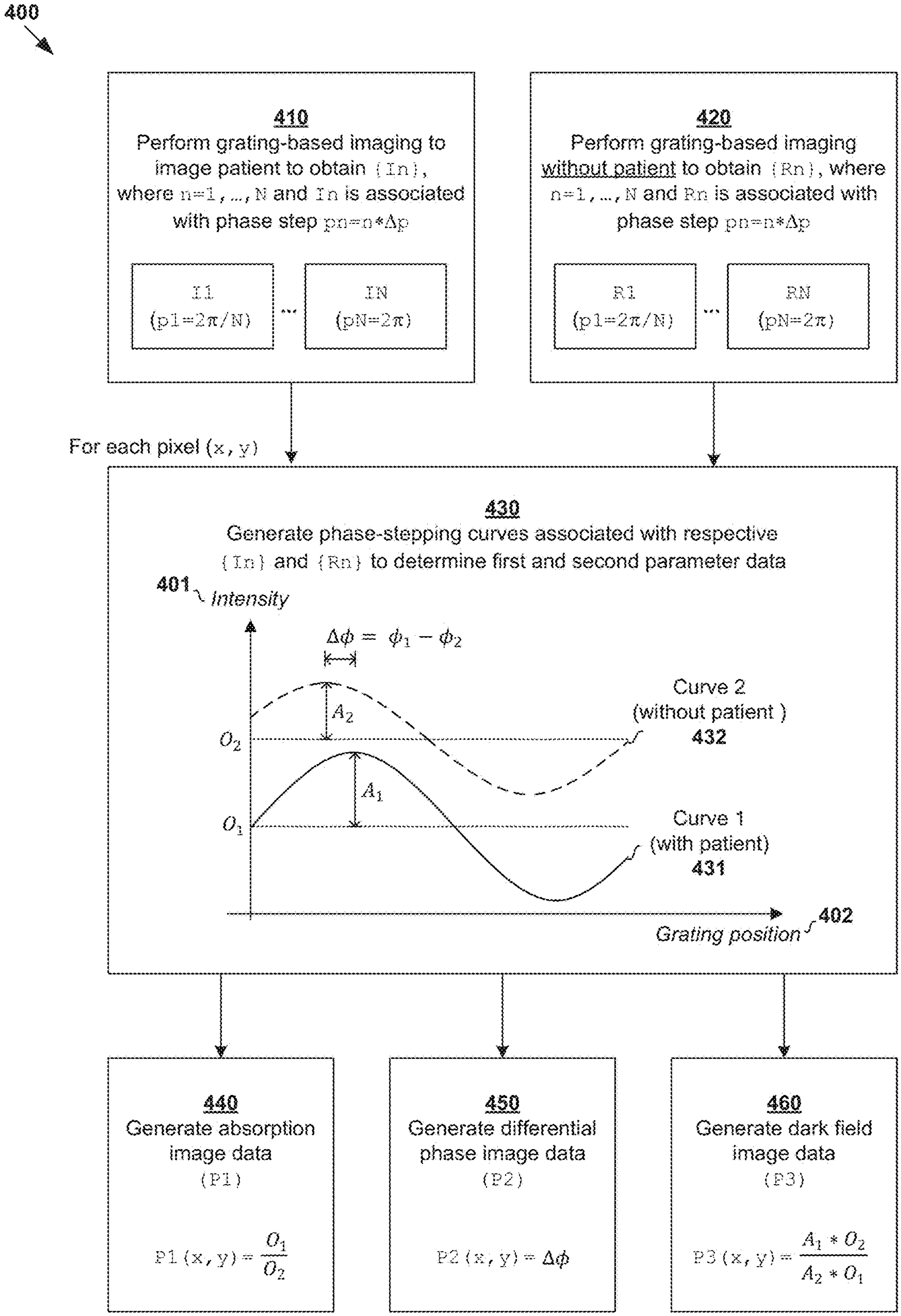
FIG. 4 is a flowchart of an example detailed process for a computer system to generate absorption image data, phase-contrast image data and dark-field image data.

At 410 in FIG. 4, computer system 160 may obtain projection image data 180 that is acquired or generated using grating-based imaging system 140 to image patient 113 during a treatment phase of radiation therapy. Using the example in FIGS. 1-2, control system 150 may generate and send control signal(s) to grating-based imaging system 140 during the imaging process. Computer system 160 may interface with detector 142 to obtain projection image data 180, which may be denoted as {∈} to represent a set of multiple (N) projection images for n=1, . . . , N.

Each projection image (¿) may be generated using imaging source 141 to emit imaging beam 143 towards multiple gratings 144-146 and detector 142. Patient 113 may be positioned between a pair of gratings, such as G0 144 and G1 145. Using phase stepping (explained using FIG. 2), each projection image (¿) may be associated with a particular phase step or grating position (pn) associated with G2 146, such as n(2π/N) using phase step size Δp=2π/N. Each projection image (¿) may represent intensity measurement data associated with multiple pixels of pixelated detector 142. A particular pixel may be denoted as (x, y).

(b) Reference Image Data (Without Patient)

At 420 in FIG. 4, computer system 160 may obtain reference image data that is generated using grating-based imaging system 140 without any patient along the beamline (i.e., no subject imaged). The reference image data may be denoted as {Rn} to represent a set of multiple (N) reference images for n=1, . . . , N. Each reference image (Rn) may include reference intensity measurement data associated with multiple pixels of pixelated detector 142. Using phase stepping, each reference image (Rn) may be associated with a particular phase step or grating position (pn) associated with G2 146, such as n(2π/N) using phase step size=2π/N.

(c) Phase-Stepping Curves

At 430 in FIG. 4, computer system 160 may determine, for a particular pixel (x, y), phase-stepping curves 431-432 associated with respective {∈} and {Rn}. In general, a phase-stepping curve is a periodic function that may be approximated using a sine function, etc. Phase-stepping curve 431-432 may each represent the intensity oscillations associated with various grating positions for a particular pixel (x, y). In the case where the intensity oscillations are sine functions, a fast Fourier transform (FFT) may be performed for each pixel (x, y) for the intensity oscillations. Alternatively, a least-squares algorithm for fitting a sine function to the data may be used.

Based on {¿}, first phase-stepping curve 431 (see "Curve 1" in FIG. 4) associated with pixel (x, y) may be generated, such as by plotting measured intensity data against its associated phase step position pn. From first phase-stepping curve 431, computer system 160 may extract first parameter data that includes ($O_1$, $A_1$, $\phi_1$), where $O_1$=first intensity offset data or mean intensity data, $A_1$=first amplitude data and $\phi_1$=first phase data.

Based on {Rn}, second phase-stepping curve 432 (see "Curve 2" in FIG. 4) associated with pixel (x, y) may be generated, such as by plotting intensity data that is measured without patient 113 against its associated phase step position pn. From second phase-stepping curve 432, computer system 160 may extract second parameter data that includes ($O_2$, $A_2$, $\phi_2$), where $O_2$=second intensity offset data or mean intensity data, $A_2$=second amplitude data and $\phi_2$=second phase data.

(d) Image Data Generation

At 440 in FIG. 4, computer system 160 may generate P1 240 for a particular pixel (x, y) based on intensity offset data=($O_1$, $O_2$) extracted from phase-stepping curves 431-432 associated with that pixel. In particular, computer system 160 may estimate $P1(x, y)=O_1/O_2$, which is a ratio between (a) the first intensity offset data ($O_1$) associated with first curve 431 (i.e., with patient) and (b) the second intensity offset data ($O_2$) associated with second curve 432 (i.e., without patient). Block 440 may be repeated for all pixels.

At 450 in FIG. 4, computer system 160 may generate P2 250 based on phase data=($\phi_1$, $\phi_2$) extracted from phase-stepping curves 431-432 associated with pixel (x, y). In particular, computer system 160 may estimate $P2(x, y)=\phi_1-\phi_2=\Delta\phi$, which represents the phase difference or phase shift between (a) the first phase data ($\phi_1$) associated with first curve 431 (i.e., with patient) and (b) the second phase data ($\phi_2$) associated with second curve 432 (i.e., without patient). $\Delta\phi$ represents a measurement parameter for P2 250. Block 450 may be repeated for all pixels.

At 460 in FIG. 4, computer system 160 may generate P3 260 based on intensity data=($O_1$, $O_2$) and amplitude data=($A_1$, $A_2$) extracted from phase-stepping curves 431-432 associated with pixel (x, y). First, computer system 160 may estimate $V_1=A_1/O_1$, which is first visibility data based on $A_1$=first amplitude data and $O_1$=first intensity offset data from first curve 431 (i.e., with patient). Next, computer system 160 may estimate $V_2=A_2/O_2$, which is second visibility data based on $A_2$=second amplitude data and $O_2$=second intensity offset data from second curve 432 (i.e., without patient). This way, computer system 160 may estimate dark-field image data associated with pixel (x, y) using $P3(x, y)=V_1/V_2=(A_1{*}O_2)/(A_2{*}O_1)$. Block 460 may be repeated for all pixels.

In practice, P1 240 (i.e., traditional X-ray images) may reveal the internal structure of soft tissue based on absorption contrast. P2 250 (i.e., phase-contrast X-ray images) may provide additional information by revealing phase changes within boundaries of target structure 210. Phase-contrast imaging may offer greater imaging sensitivity compared to conventional absorption-based imaging, particularly for low-density or low-absorbing materials. P3 260 (i.e., dark-field X-ray images) may provide additional information by revealing structures that scatter X-rays, such as microstructures within soft tissue, etc.

Although explained using FIG. 4, it should be understood that any additional and/or alternative techniques may be used for image data generation. For example, techniques for exploiting moiré patterns may be implemented to generate P2 250 and/or P3 260. In general, moiré patterns are interference patterns that may occur when two regular patterns (e.g., gratings) overlap and interfere with each other. The moiré patterns may be residual or introduced on purpose.

(e) Motion Artifacts

According to examples of the present disclosure, motion artifacts that are considered to be a disadvantage for diagnostic imaging (i.e., pre-treatment phase) may be exploited for target structure tracking. Here, the term "motion artifact" may refer generally to image data degradation that is caused by patient motion during image acquisition. The motion may be voluntary or involuntary (e.g., respiration or cardiac motion). In practice, any movement (e.g., in the order of micrometers) of target structure 210 during one phase step, or between multiple phase steps, may result in motion artifacts at the border of target structure 210. These motion artifacts may be exploited to solve the task of motion detection more efficiently. Depending on the desired implementation, motion artifacts may also speed up the image acquisition process.

An example will be explained using FIG. 5, which is example diagram 500 illustrating example phase stepping curves 540-560 that are generated based on projection image data 510-530 and reference image data 520. Here, first projection image data 510 may be a set of first images that are denoted as {∈} for n=1, . . . , N and respective grating positions. Similar to the example in FIG. 4, {¿} may be generated using grating-based imaging system 140 to image target structure 210 within patient 113 who is positioned in a beam line associated with imaging beam 143 (see FIG. 2). Based on {¿}, first phase stepping curve 540 (see "Curve 1") may be generated.

Reference image data 520 may be a set of reference images that are denoted as {Rn} for n=1, . . . , N and respective grating positions (pn). Similar to the example in FIG. 4, {Rn} may be generated using grating-based imaging system 140 without patient 113 in a beam line associated with imaging beam 143 (see FIG. 2). Based on {Rn}, second phase stepping curve 550 (see "Curve 2") may be generated.

Second projection image data 530 may be a set of second images that are denoted as {Jn} and generated using grating-based imaging system 140 with patient 113 in the beam line. Based on {Jn}, third phase stepping curve 560 (see "Curve 3") may be generated. Compared with {¿}, patient 113 may have moved during the imaging process, thereby introducing motion artifact(s) into {Jn}. For example, target structure 210 of patient 113 may move out of the beam line between grating positions 8 and 9 (see 570 in FIG. 5).

For a first case (i.e., substantially low motion or no motion), image data generation may be performed based on parameter data extracted from "Curve 1" 540 and reference "Curve 2" 550, such as P1=0.6, P2=0.4 and P3=1.33 for a particular pixel (x, y). For a second case (i.e., with motion), image data generation may be performed based on parameter data extracted from "Curve 3" 560 and reference "Curve 2" 550, such as P1'=0.65, P2'=0.89 and P3'=1.57 for a particular pixel (x, y). Comparing these values to neighboring pixel (x', y') associated with air only (to get the contrast), (ΔP1=0.4, ΔP2=0.4, ΔP3=0.33) for the first case and (ΔP1'=0.35, ΔP2'=0.89, ΔP3'=0.57) for the second case.

Figure 5:
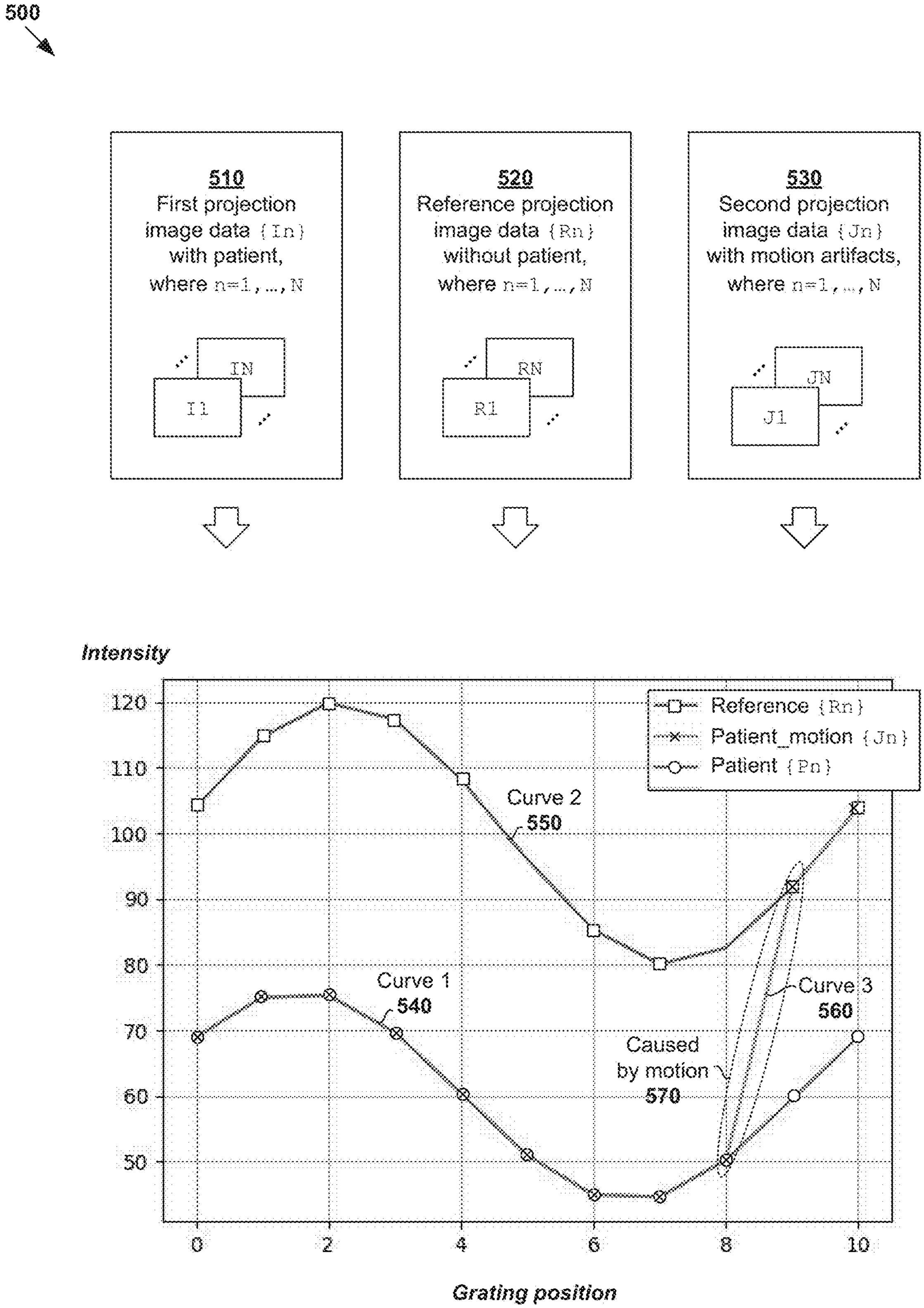
FIG. 5 is a diagram illustrating example phase-stepping curves that are generated based on projection image data and reference image data.

Based on the example in FIG. 5, it may be observed that motion artifacts introduced by patient 113 may result in an increased contrast compared to air at the boundary in the second case when compared to the first case. Such change in signal (or contrast) compared to a prior measurement in a series of measurements may be exploited to detect patient movement. This is similar to the classical attenuation-based "digital subtraction imaging" technique.

Example Target Structure Tracking

Blocks 330-340 in FIG. 3 will be explained further using FIG. 6, which is a schematic diagram illustrating example process 600 for processing image data and generating derived image data for target structure tracking.

(a) Metric-Based Selection

Figure 6:
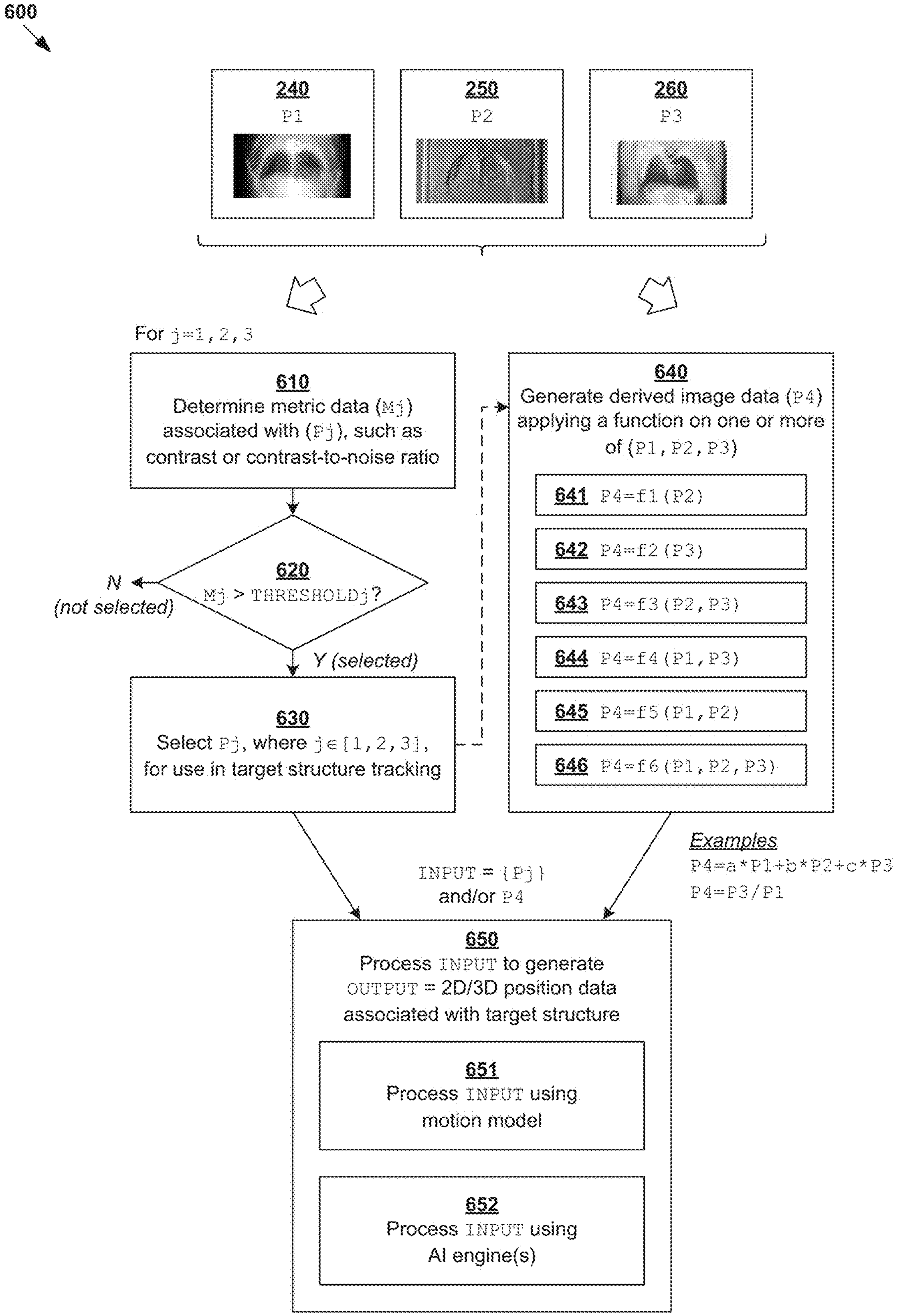
FIG. 6 is a flowchart illustrating an example detailed process for processing image data and generating derived image data for target structure tracking.

At 610-630 in FIG. 6, computer system 160 may implement a metric-based approach to select at least P2 250 and/or P3 260 for subsequent target structure tracking. For a particular P j, computer system 160 may determine metric data (Mj) associated with P j. Any suitable metric data may be determined, such as contrast, contrast to noise ratio, etc. In response to determination that M j satisfies a particular threshold (e.g., first threshold for contrast or second threshold for contrast-to-noise ratio exceeded), associated P j may be selected. Note that j[1, 2, 3] representing P1 240 (j=1), P2 250 (j=2) and P3 260 (j=3). This way, selected P j may be used to track motion of target structure 210 during radiation treatment.

In one example, in response to determination that first metric data (M2) associated with P2 250 satisfies a first threshold, P2 250 may be selected for use in subsequent position data estimation during target structure tracking. Additionally or alternatively, in response to determination that second metric data (M3) associated with P3 260 satisfies the first threshold or a second threshold, P3 260 may be selected for use in subsequent position data estimation during target structure tracking.

(b) Derived Image Data

Additionally or alternatively, at 640 in FIG. 6, computer system 160 may generate P4=derived image data based on at least one of P1 240, P2 250 and P3 260 according to blocks 641-646. At 641-642 in FIG. 6, computer system 160 may generate P4 by applying a function on one type of image data. For example, first function=f1(P2) may be applied to process P2 250 only. In another example, second function=f2(P3) may be applied to process P3 260 only. Blocks 641 and/or 642 may be performed to derive an absolute value for each pixel in image data 250/260, or threshold the value according to any suitable approach.

At 643-646 in FIG. 6, computer system 160 may generate P4 by applying a function on at least two of P1 240, P2 250 and P3 260. One or more of the following may be used: P4=f3(P1, P2, P3), P4=f4(P1, P2), P4=f5(P1, P3) and P4=f6 (P2, P3). Any suitable function may be applied, such as linear combination function, non-linear combination function, ratio function, etc. A first linear combination function to combine or fuse various image data may be in the form of P4=a*P1+b*P2+c*P3 using coefficients (a, b, c). Another second example linear combination function may be in the form of P4=f4(P2, P3)=b*P2+c*P3. In another example, P4=f3(P1, P3)=P3/P1 may be determined. Since P1 is a measure of absorption and P3 is a measure of scattering power, P4 may be described as scattering power per absorption. This measure may be used to facilitate the differentiation between different types of tissues.

(c) Target Structure Tracking

At 650 in FIG. 6, computer system 160 may perform target structure tracking by processing input data that includes at least one of P2 250, P3 260 and P4 using any suitable approach, such as an image processing pipeline (see 651) or artificial intelligence (AI) engine or engines (see 652). In one example, P4=f5(P2) may be used as an input segmentation mask for later steps in an image processing pipeline (e.g., in a non-analytic way) to perform image processing other image data (e.g., P1 240, P2 250 or P4) selective on the pixel-wise values of P2 250. In this case, since P2 250 is a differential image, it may be used as a segmentation mask to identify the boundaries of target structure 210. The segmentation mask may be used in later steps that require information on the edges (e.g., edge enhancement algorithm) to process only certain image areas.

Additionally or alternatively, the image processing pipeline may implement a tracking algorithm based on computer vision to localize target structure 210 in 2D (or 3D in the case where stereoscopic images are available). Some examples will be discussed with reference to FIG. 7, which is a schematic diagram illustrating example position data estimation 700 using an image processing pipeline that includes motion model 720. The example in FIG. 7 may be implemented by computer system 160 using any suitable computer vision or target tracking algorithm. One example algorithm is described with reference to conventional absorption image data (e.g., 2D kV images) in an article entitled "Real-time volumetric image reconstruction and 3D tumor localization based on a single x-ray projection image for lung cancer radiotherapy," by Li R, Jia X, Lewis J H, Gu X, Folkerts M, Men C, Jiang S B, Med Phys. 2010 June; 37(6): 2822-6. This article is incorporated herein by reference.

During a training phase (see 701), motion model 720 may be trained using V0=reference volume image data 710 that is acquired prior to the treatment phase. For example, in the case of lung tumor localization, V0 710 may include a set of volumetric images (e.g., planning CT) of patient 113 at multiple (K) breathing phases. Based on V0 710, deformable image registration may be performed between a reference phase and the other K−1 phases, resulting in parameter data 721 in the form of deformation vector fields (DVFs). The set of DVFs may be represented using eigenvectors and coefficients obtained from principal component analysis (PCA). By varying the PCA coefficients, new DVFs may be generated. When applied on V0 710, new volume image data (also known as 3D configuration) may be generated as follows.

During a tracking phase (see 702) while treatment is delivered, computer system 160 may apply motion model 720 to generate output data=V1 (see 740) based on input data={P j}. In more detail, at 730 in FIG. 7, input data={P j} may be 2D projection image data that is acquired during a treatment phase, where P j for j∈[1, . . . , 3] may be selected at block 630 in FIG. 6 and/or P4 derived at block 640 in FIG. 6. At 740 in FIG. 7, output data=V1 may represent simulated volume image data (3D) whose corresponding simulated projection image data (2D) best matches with the input data measured or derived in real time. Using this approach, the input data (i.e., real-time 2D projection image data) may be used to optimize parameter data 721 of motion model 720. The idea here is that the output data representing the correct or best-fit 3D configuration will result in simulated projection image data that best matches with the input projection image data.

The result of the optimization or "fit" of motion model 720 may then be applied to the reference CT image, thereby propagating and effectively localizing the target voxels. For example, at 750 in FIG. 7, computer system 160 may determine 3D position data denoted as 3D1=(x, y, z) associated with target structure 210 based on V1=simulated volume image data (see 740) and V0=reference volume image data (see 710). Depending on the desired implementation, the 3D position data estimation may involve performing deformation inversion (e.g., applying inverted DVF) to calculate 3D1. In practice, this approach may rely on high-performance graphics processing unit (GPU) computational hardware to achieve real-time performance.

Figure 7:
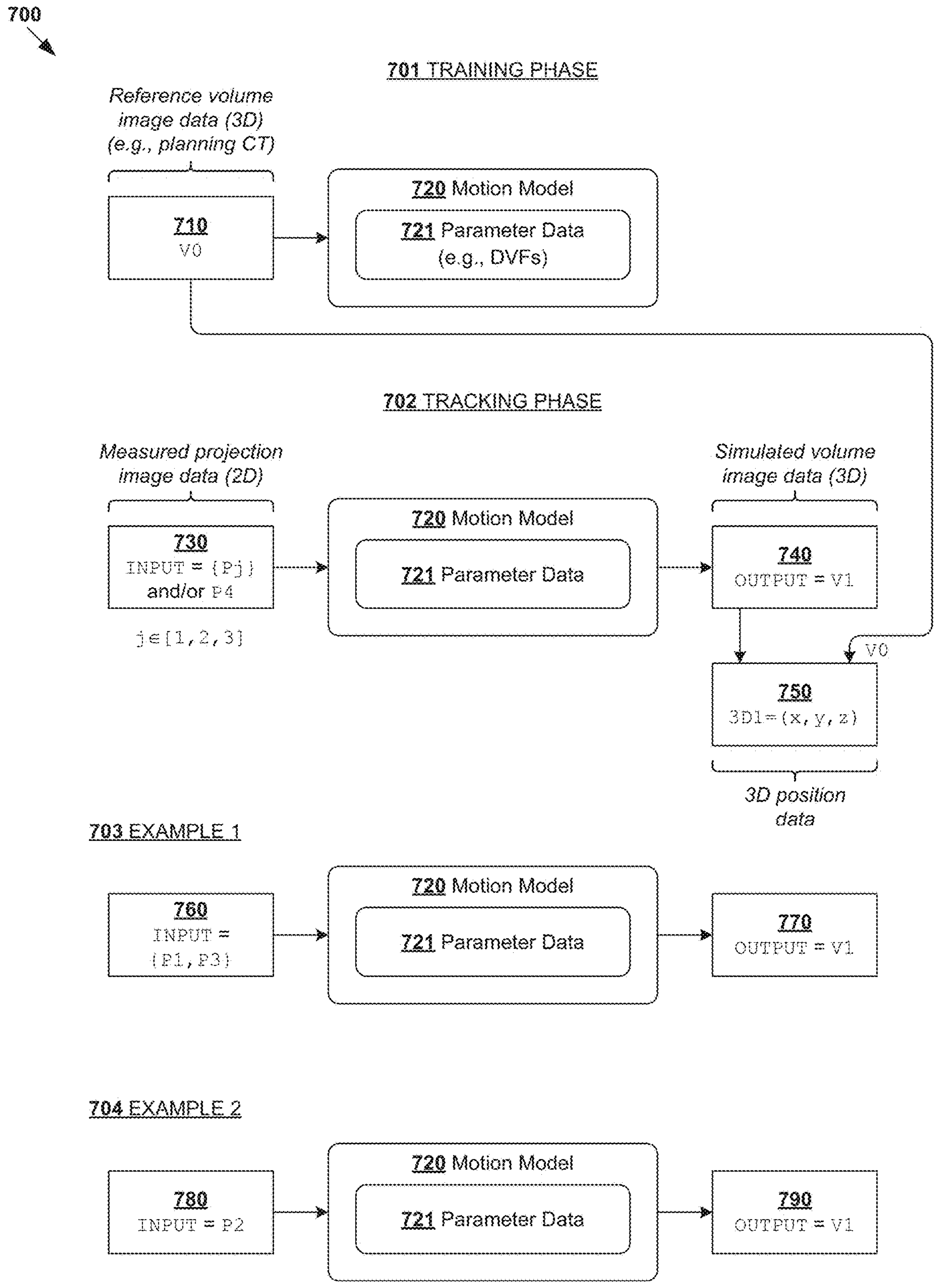
FIG. 7 is a schematic diagram illustrating an example detailed process for position data estimation using an image processing pipeline that includes a motion model.

According to examples of the present disclosure, improved tracking accuracy may be achieved using input data that includes P2 250 (i.e., phase contrast image data), P3 260 (i.e., dark field image data), or any derivation thereof. This may in turn lead to better treatment outcomes, where target dose coverage may be effectively maintained while shrinking margins and increasing safety (especially for hypo-fractionated treatments). Two examples are shown in FIG. 7. In a first example (see 703), input data 760 may include P1 240 (i.e., absorption image data) that is augmented with P3 260. In this case, output data=V1 770 generated using motion model 720 may result from the best match (or fit) between pre-calculated and measured data for both kV absorption and dark field image data. In a second example (see 704), input data 780 that includes P2 250 may be mapped to output data=V1 790. This helps to better localize periodic motion on a hysteresis curve (e.g., 3D configurations may be similar but moving in opposite directions, which would be apparent on phase contrast image). The use of phase contrast image data may lead to better motion prediction results and/or detection of beam interlocks for sudden fast motion (e.g., coughing).

Depending on the desired implementation, any suitable variations to the example in FIG. 7 may be implemented. For example, some algorithms have more complex or realistic motion models. In another example, instead of performing the "fitting" step, some algorithms may use a "lookup" approach to perform a quick nearest neighbor search or interpolated lookup on a library of pre-calculated 2D kV images associated with a variety of possible 3D configurations. The "lookup" approach may be replaced by a deep neural network (pre-trained on a specific patient, or general population) to take as input a 2D kV image data and output a 3D configuration (including target voxel labeling). Other variations include 2D MV portal images (during treatment) in place of, or supplemental to, the 2D kV image data.

During tracking phase 702, the calculated 3D configuration (i.e., output data 740/770/790) may be compared with the original planning CT configuration (see 710). Margins may be set to shut off treatment beam 130 when target structure 210 is detected to have moved outside of some pre-set margin. The margin may be set by the integrated target volume (ITV) in 3D or ITV projection onto 2D beam's eye view (to be compared to the MLC aperture). The desired implementation may depend on the specific modality, such as step and shoot or sliding window IMRT, conformal arc, or VMAT. In some cases, the algorithm is designed to adjust the delivery on the fly (MLC tracking), such algorithms often require predicting the motion into the future due to the latency in image acquisition, calculation, and MLC signaling and speed limitations.

AI-Based Approach

At 652 in FIG. 6, computer system 160 may perform target structure tracking by processing at least one of P2 250, P3 260 and P4 using an AI engine. As used herein, the term "AI engine" may refer to any suitable hardware and/or software component(s) of a computer system that are capable of executing algorithms according to any suitable AI model(s). Depending on the desired implementation, an "AI engine" may be a machine learning engine based on machine learning model(s), deep learning engine based on deep learning model(s), etc. In general, deep learning is a subset of machine learning in which multi-layered neural networks may be used for feature extraction as well as pattern analysis and/or classification.

Depending on the desired implementation, any suitable AI model(s) may be used, such as convolutional neural network, recurrent neural network, deep belief network, generative adversarial network (GAN), autoencoder(s), variational autoencoder(s), long short-term memory architecture for tracking purposes, generative AI model, or any combination thereof, etc. In practice, a neural network is generally formed using a network of processing elements (called "neurons," "nodes," etc.) that are interconnected via connections (called "synapses," "weight data," etc.). A processing layer of a convolutional neural network may be a convolutional layer, pooling layer, un-pooling layer, rectified linear units (ReLU) layer, fully connected layer, loss layer, activation layer, dropout layer, transpose convolutional layer, concatenation layer, or any combination thereof, etc. For example, convolutional neural networks may be implemented using any suitable architecture(s), such as UNet, LeNet, AlexNet, ResNet, VNet, DenseNet, OctNet, etc.

Figure 8A:
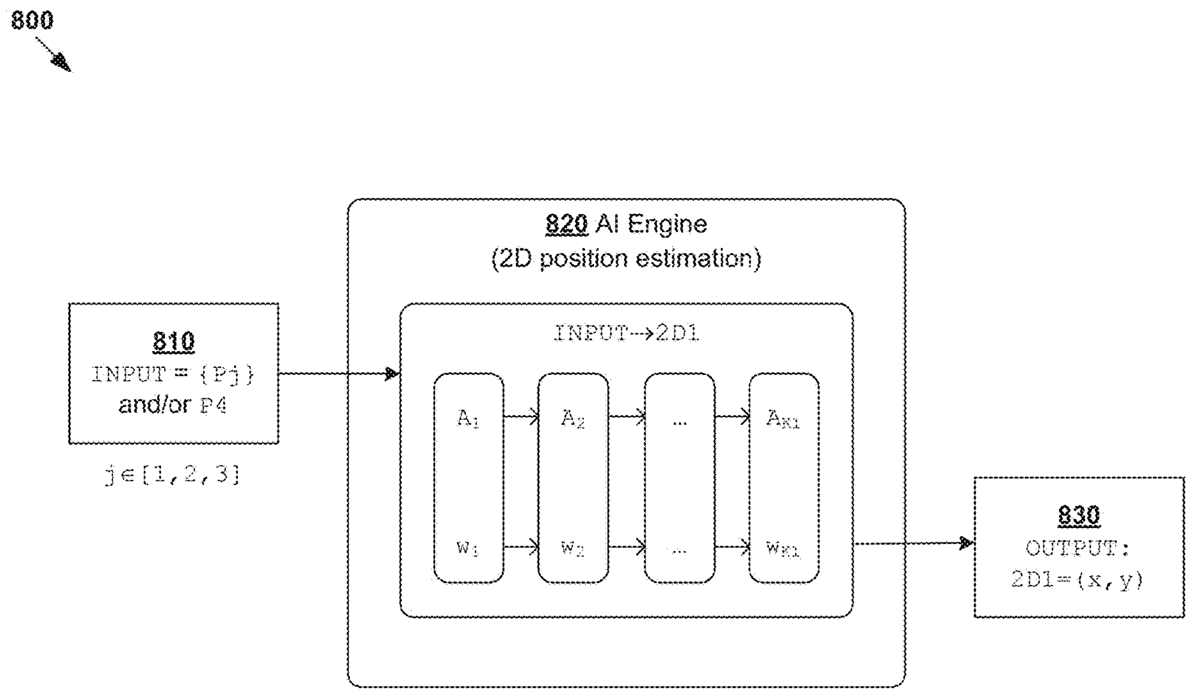
FIG. 8A is a schematic diagram illustrating an example two-dimensional (2D) position data estimation using a first artificial intelligence (AI) engine.

FIG. 8A is a schematic diagram illustrating example 2D position data estimation 800 using first AI engine 810. Here, first AI engine 810 may be implemented to process and map (a) input data={P j}, where j∈[1, . . . , 3], selected at block 630 in FIG. 6 and/or P4 derived at block 640 in FIG. 6 to (b) output data=2D position data denoted as 2D1=(x, y) associated with target structure 210. First AI engine 810 may include a hierarchy of multiple (K1) processing layers (denoted as $A_1$ to $A_{K1}$), such as an input layer, an output layer, and multiple (i.e., two or more) "hidden" layers between the input and output layers. The processing layers ($A_1$ to $A_{K1}$) are associated with respective weight data ($w_1$ to $w_{K1}$). During training, first AI engine 820 may learn weight data ($w_1$ to $w_{K1}$) to perform 2D position data estimation based on the input data.

Figure 8B:
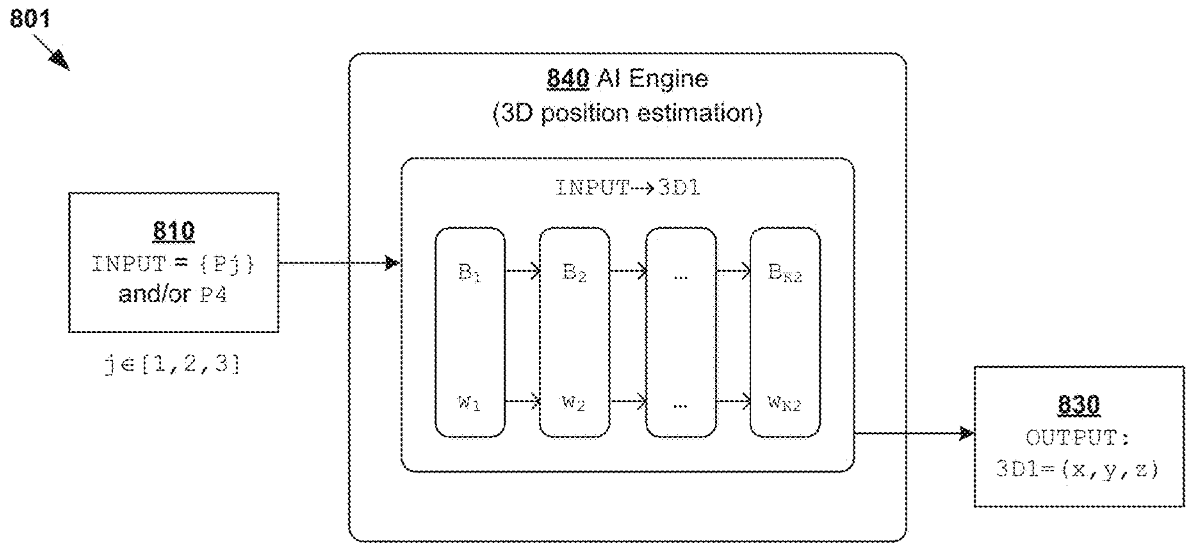
FIG. 8B is a schematic diagram illustrating an example three-dimensional (3D) position data estimation using a second AI engine.

FIG. 8B is a schematic diagram illustrating example 3D position data estimation 801 using second AI engine 840. Here, second AI engine 840 may be implemented to process (a) input data={P j} selected at block 630 in FIG. 6 and/or P4 derived at block 640 in FIG. 6 and map the input data to (b) output data=3D position data denoted as 3D1=(x, y, z) associated with target structure 210. Similarly, second AI engine 840 may include a hierarchy of multiple (K2) processing layers (denoted as $B_1$ to $B_{K1}$). During training, second AI engine 840 may learn weight data ($w_1$ to $w_{K1}$) associated with the processing layers ($B_1$ to $B_{K1}$) to perform 3D position data estimation based on the input data.

Deep learning engine 810/840 may be trained using any suitable approach, such as supervised learning, unsupervised learning, semi-supervised learning, reinforcement learning, etc. For example, in supervised learning, deep learning engine 810/840 may be trained on a dataset of labeled examples in order to learn the relationship between input data=image data (e.g., phase-contrast, dark-field, derived, or any combination thereof) showing at least part of a target structure and output=2D/3D position data associated with the target structure. Any suitable training data may be used, such as synthetic data such as digitally reconstructed radiographs (DRRs), real patient data, or a combination of both. Deep learning engine 810/840 may be trained using training data that is specific to patient 113, or a large variation of possible patients. In practice, a patient-specific training strategy may tackle the issue of inter-patient and inter-tumor variations (e.g., tumor size, shape, location, motion). In this case, DRRs may be synthetically generated for every degree of a full gantry arc (360°).

Alternatively, in unsupervised learning, deep learning engine 810/840 may be trained on a dataset of unlabeled examples in order to learn patterns and relationships in the data without any prior knowledge of the output labels. In semi-supervised learning, both labeled and unlabeled data may be used. Semi-supervised learning is useful in situations where there is a large amount of unlabeled data available, but it might be too expensive or difficult to label all of it. In reinforcement learning, deep learning engine 810/840 may learn to perform 2D/3D position data estimation by trial and error where it is rewarded for taking actions that lead to desired outcomes and penalized for taking actions that lead to undesired outcomes.

Example Treatment Planning and Delivery

According to examples of the present disclosure, target structure tracking may be performed based on phase-contrast and/or dark-field image data to improve tracking accuracy. An example use case will be explained using FIG. 9, which is a flowchart of example detailed process 900 for treatment planning and delivery that includes target structure tracking based on phase-contrast and/or dark-field image data. Example process 900 may include one or more operations, functions, or actions illustrated by one or more blocks, such as 910 to 995. Depending on the desired implementation, various blocks may be combined into fewer blocks, divided into additional blocks, and/or eliminated. In the example in FIG. 9, radiotherapy treatment may include (a) a treatment planning phase (see 901) that involves generating a suitable treatment plan (see 930) for patient 113 and (b) a treatment delivery phase (see 902) that involves delivering treatment according to the treatment plan.

(a) Treatment Planning Phase

Examples of the present disclosure may be implemented during any suitable radiation therapy, such as stereotactic body radiation therapy (SBRT) for lung cancer treatment, etc. SBRT is a type of radiation therapy that delivers a high dose of radiation to a relatively small area of the body. For example, tumor tracking during lung SBRT may help to verify patient positioning during treatment to reduce the probability of a geographic miss by confirming that a tumor remains inside a planning target volume (PTV). In the following, an example target structure will be discussed with reference to a tumor. It should be noted that any other target structure(s) may be tracked.

At 910 in FIG. 1, image data acquisition may be performed to capture planning projection image data 910 (denoted as "P0) associated with patient 113 (particularly the patient's anatomy). Any suitable medical image modality or modalities may be used, such as computed tomography (CT), magnetic resonance imaging (MRI), cone beam computed tomography (CBCT), positron emission tomography (PET), magnetic resonance tomography (MRT), single photon emission computed tomography (SPECT), any combination thereof, etc. For example, when CT or MRI is used, P0 910 may include a series of 2D images or slices, each representing a cross-sectional view of the patient's anatomy; volumetric or 3D images of the patient; or a time series of 2D or 3D images of the patient (e.g., four-dimensional (4D) CT or 9D CBCT). In practice, P0 910 may include transverse, coronal, and sagittal slices of the patient's anatomy.

Figure 9:
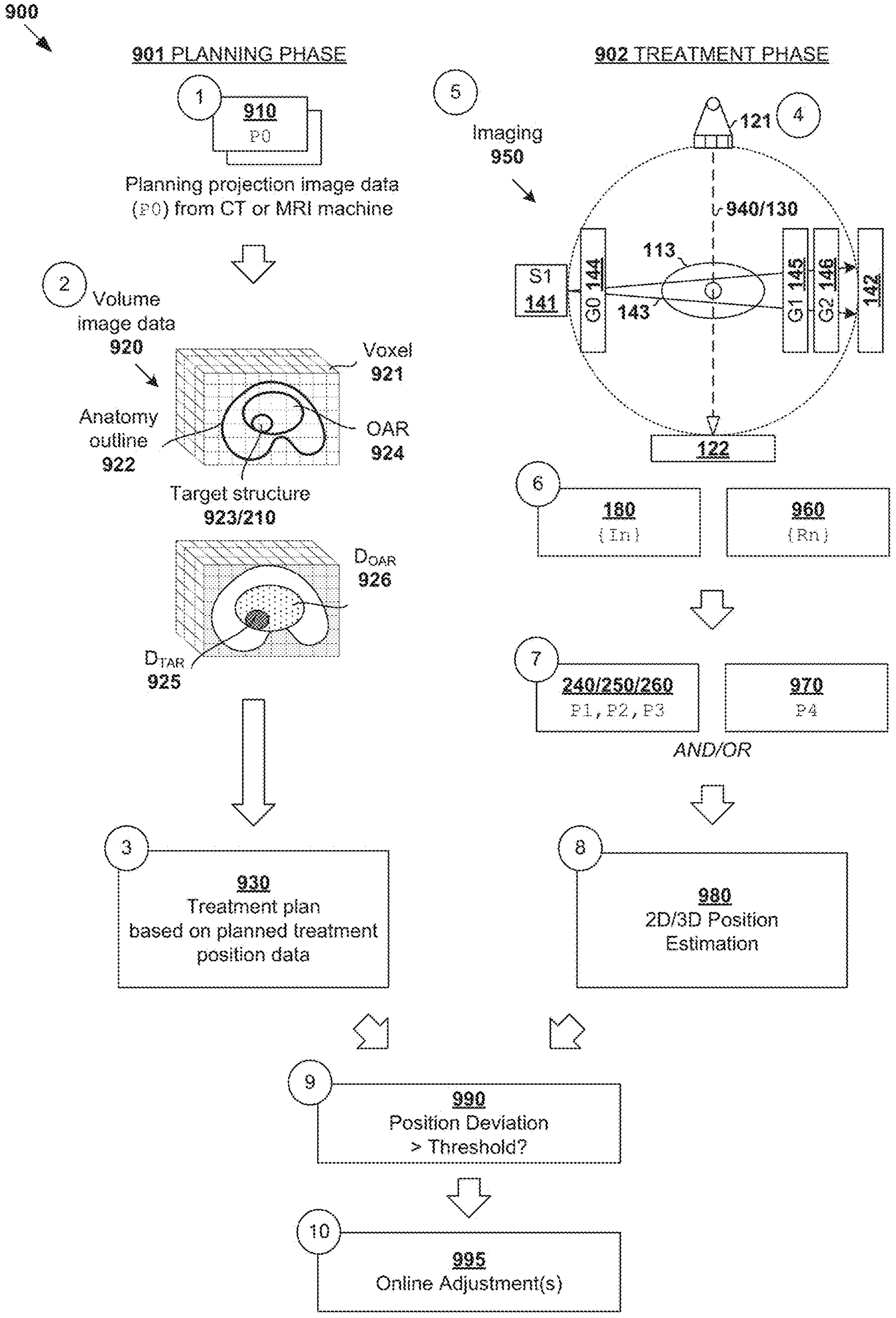
FIG. 9 is a schematic diagram illustrating an example detailed process for treatment planning and delivery that includes target structure tracking based on phase-contrast and/or dark-field image data.

At 920 in FIG. 9, treatment planning may be performed to, inter alia, generate a treatment plan that delivers a certain high dose to a target structure while delivering a lower dose to the OAR. For example, segmentation (e.g., automated or manual) may be performed to generate volume image data 920 identifying various segments or structures based on P0 910. Volume image data 920 (also known as a digital or treatment volume) may be divided into multiple smaller volume-pixels (voxels) 921. Each voxel 921 may represent a 3D element within the treatment volume. Volume image data 920 may also include any suitable data relating to the contour, shape, size, and location of patient's anatomy 922, target structure 923 (e.g., tumor), OAR 924, or any other structure of interest (e.g., tissue, bone).

Further, dose calculation may be performed based on P0 910 and/or volume image data 920 to generate dose data specifying radiation doses to be delivered to target structure 923 (denoted "DTAR" at 925) and OAR 924 (denoted "DOAR" at 926). For example, target structure 923 (210 in FIG. 2) may represent a malignant tumor requiring radiotherapy treatment, such as lung tumor, prostate tumor, etc. OAR 924 may be a proximal healthy structure that might be adversely affected by the treatment, such as central airway, rectum, bladder, etc. Target structure 923 is also known as a PTV. In practice, treatment volume 920 may include multiple targets 923 and OARs 924 with complex shapes and sizes. Although shown as having a regular shape (e.g., cube), voxel 921 may have any suitable shape (e.g., non-regular). Any additional and/or alternative data may be used, such as prescription data, disease staging data, biologic or radiomic data, genetic data, assay data, biopsy data, past treatment or medical history, any combination thereof, etc.

At 930 in FIG. 9, a treatment plan may be generated, such as based on a planned treatment position in 3D (denoted as 3D0) associated with target structure 923 that is estimated from P0 910 and volume image data 920. Depending on the desired implementation, treatment plan 930 may be generated to include 2D fluence map data for a set of beam orientations or angles. Each fluence map may specify the intensity and shape (e.g., as determined by an MLC) of a radiation beam emitted from a radiation source at a particular beam orientation and at a particular time. For example, IMRT or any other treatment technique(s) may involve varying the shape and intensity of the radiation beam while at a constant gantry and couch angle. Alternatively or additionally, treatment plan 930 may include machine control point data (e.g., jaw and leaf positions), VMAT trajectory data for controlling a treatment delivery system, etc. In practice, treatment plan 930 may be generated based on goal doses prescribed by a clinician (e.g., oncologist, dosimetrist, planner, etc.), such as based on the clinician's experience, the type and extent of the tumor, patient geometry and condition, etc. In practice, template(s) 935 may be generated from volume image data 920 used for treatment planning, the contours of the target, isocenter of treatment plan 930, etc.

(b) Treatment Delivery Phase

During treatment delivery phase 902, treatment plan 930 for patient 113 may be provided to radiation therapy system 100 in FIG. 1. Based on treatment plan 930, control system 150 in FIG. 1 may provide instruction(s) or control signal(s) 151 to, for example, to position LINAC 121 to apply a radiation dose to target structure 923 (i.e., tumor) while minimizing radiation dose to OAR 924, etc. Before treatment begins, patient 113 may be positioned in a supine position on treatment couch 112. To verify that patient 113 is in the correct position for treatment, image registration may be performed during patient setup.

In one example, imaging source 141 and detector 142 may be used to capture treatment projection image data such that the patient's current position on treatment couch 112 may be compared or registered against their planned treatment position. Where necessary, patient 113 may be repositioned to ensure that treatment is delivered to the intended target. During treatment delivery, gantry 110 may be rotated around patient 113 to deliver therapeutic radiation dose 940/130 to target structure 923 at various beam orientations according to treatment plan 930.

At 950 in FIG. 9, kV imaging using grating-based imaging system 140 may be performed during MV delivery to generate projection image data 180 (i.e., with patient) and reference image data 960 (i.e., no patient). This way, computer system 160 may process projection image data 180 and reference image data 960 to generate P1 240, P2 250, P3 260 and P4 970 (i.e., derived image data) according to the examples in FIGS. 4-6. At 980, computer system 160 may process any combination of P1 240, P2 250, P3 260 and P4 970 to estimate 2D/3D position data associated with target structure 923. See example tracking approaches in FIG. 7 to FIG. 8B.

At 990-995 in FIG. 9, computer system 160 may determine whether adjustment(s) are needed by comparing (a) the estimated position data calculated at block 980 with the (b) planned treatment position data based on which treatment plan 930 is generated. In response to determination that the difference/deviation exceeds a predetermined threshold, computer system 160 may generate an alert that an adjustment is required. A deviation that exceeds the predetermined threshold may indicate that a significant portion of target structure 923 is extending outside of a threshold region.

Based on the deviation detected, computer system 160 may determine or estimate adjustment(s) to the patient setup (e.g., position or orientation of couch 112) and/or treatment beam 940/130 (e.g., gantry angle, collimator setup). Alternatively or additionally, instructions may be provided to patient 113 about the depth of breathing or depth of a breath hold in order to achieve the best match between treatment geometry (i.e., current 3D position data) and the planned geometry (i.e., planned treatment position data). Where applicable, treatment may be aborted. Using examples of the present disclosure, positional verification and target structure may be performed during radiation treatment in an improved manner to identify patients who move more than a predetermined threshold. This in turn enables adjustment(s) during treatment delivery phase 902 to achieve better treatment outcomes for patient 113.

Computer System

The above examples can be implemented by hardware (including hardware logic circuitry), software or firmware or a combination thereof. The above examples may be implemented by any suitable computing device, computer system, etc. The computer system may include processor(s), memory unit(s) and physical NIC(s) that may communicate with each other via a communication bus, etc. Examples of the present disclosure may also include a non-transitory computer-readable storage medium that includes a set of instructions which, in response to execution by a processor of the computer system, cause the processor to perform target structure tracking described herein with reference to the drawings.

The techniques introduced above can be implemented in special-purpose hardwired circuitry, in software and/or firmware in conjunction with programmable circuitry, or in a combination thereof. Special-purpose hardwired circuitry may be in the form of, for example, one or more application-specific integrated circuits (ASICs), programmable logic devices (PLDs), field-programmable gate arrays (FPGAs), and others. The term 'processor' is to be interpreted broadly to include a processing unit, ASIC, logic unit, or programmable gate array etc.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or any combination thereof.

Those skilled in the art will recognize that some aspects of the embodiments disclosed herein, in whole or in part, can be equivalently implemented in integrated circuits, as one or more computer programs running on one or more computers (e.g., as one or more programs running on one or more computing systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Software to implement the techniques introduced here may be stored on a non-transitory computer-readable storage medium and may be executed by one or more general-purpose or special-purpose programmable microprocessors. A "computer-readable storage medium", as the term is used herein, includes any mechanism that provides (i.e., stores and/or transmits) information in a form accessible by a machine (e.g., a computer, network device, personal digital assistant (PDA), mobile device, manufacturing tool, any device with a set of one or more processors, etc.). A computer-readable storage medium may include recordable/non recordable media (e.g., read-only memory (ROM), random access memory (RAM), magnetic disk or optical storage media, flash memory devices, etc.).

The drawings are only illustrations of an example, wherein the units or procedure shown in the drawings are not necessarily essential for implementing the present disclosure. Those skilled in the art will understand that the units in the device in the examples can be arranged in the device in the examples as described or can be alternatively located in one or more devices different from that in the examples. The units in the examples described can be combined into one module or further divided into a plurality of sub-units.

The invention claimed is:

1. A method for a computer system to perform target structure tracking for radiation therapy, wherein the method comprises:

obtaining projection image data that is generated using an imaging source to emit an imaging beam towards a patient and a detector to image a target structure within the patient during a treatment phase of radiation therapy;

based on the projection image data, generating at least one of (a) phase-contrast image data associated with the target structure and (b) dark-field image data associated with the target structure; and determining position data associated with the target structure by processing at least one of the following: (a) the phase-contrast image data, (b) the dark-field image data and (c) derived image data that is generated based on the phase-contrast image data or the dark-field image data, thereby tracking the target structure during the treatment phase of the radiation therapy, wherein determining position data associated with the target structure comprises:

determining first metric data associated with the phase-contrast image data and second metric data associated with the dark-field image data;

in response to determination that the first metric data satisfies a first threshold, selecting the phase-contrast image data for use in determining the position data; and in response to determination that the first metric data does not satisfy the first threshold, excluding the phase-contrast image data from use in determining the position data; and in response to determination that the second metric data satisfies the first threshold or a second threshold, selecting the dark-field image data for use in determining the position data; and in response to determination that the second metric data does not satisfy either the first threshold or the second threshold, excluding the dark-field image data from use in determining the position data.

2. The method of claim 1, wherein obtaining the projection image data comprises:

obtaining the projection image data that is generated using a grating-based imaging system that includes the imaging source, the detector and multiple gratings that are positioned between the imaging source and the detector.

3. The method of claim 2, wherein generating at least one of (a) the phase-contrast image data and (b) the dark-field image data comprises:

determining first parameter data associated with the projection image data that includes a set of multiple projection images associated with a set of respective multiple phase steps, wherein the first parameter data includes first intensity offset data, first amplitude data and first phase data;

determining second parameter data associated with reference image data that is generated using the grating-based imaging system without the patient, wherein the reference image data includes a set of multiple reference images associated with the set of respective multiple phase steps, wherein the second parameter data includes second intensity offset data, second amplitude data and second phase data; and based on the first parameter data and the second parameter data, generating (a) the phase-contrast image data, (b) the dark-field image data and (c) absorption image data.

4. The method of claim 1, wherein the method further comprises:

generating the derived image data by applying a function to combine or calculate a ratio between at least two of the following: (a) the phase-contrast image data, (b) the dark-field image data and (c) absorption image data.

5. The method of claim 1, wherein determining the position data comprises:

based on a motion model associated with the target structure, generating three-dimensional (3D) volume image data associated with at least one of the following two-dimensional (2D) projection image data: (a) the phase-contrast image data, (b) the dark-field image data and (c) the derived image data; and determining 3D position data associated with the target structure based on (a) reference 3D volume image data acquired prior to the treatment phase and (b) the generated 3D volume image data.

6. The method of claim 1, wherein determining the position data comprises:

determining 2D or 3D position data associated with the target structure using an artificial intelligence (AI) engine to process at least one of the following: (a) the phase-contrast image data, (b) the dark-field image data and (c) the derived image data, wherein the AI engine includes multiple processing layers that are trained to perform position data estimation.

7. A computer system, comprising:

a processor; and a non-transitory computer-readable medium having stored thereon instructions that, when executed by the processor, cause the processor to perform the following:

obtain projection image data that is generated using an imaging source to emit an imaging beam towards a patient and a detector to image a target structure within the patient during a treatment phase of radiation therapy;

based on the projection image data, generate (a) phase-contrast image data associated with the target structure and (b) dark-field image data associated with the target structure; and determine position data associated with the target structure by processing at least one of the following: (a) the phase-contrast image data, (b) the dark-field image data and (c) derived image data that is generated based on the phase-contrast image data or the dark-field image data, thereby tracking the target structure during the treatment phase of the radiation therapy, wherein the instructions for determining position data associated with the target structure cause the processor to:

determine first metric data associated with the phase-contrast image data and second metric data associated with the dark-field image data;

in response to determination that the first metric data satisfies a first threshold, select the phase-contrast image data for use in determining the position data; and in response to determination that the first metric data does not satisfy the first threshold, exclude the phase-contrast image data from use in determining the position data; and in response to determination that the second metric data satisfies the first threshold or a second threshold, select the dark-field image data for use in determining the position data; and in response to determination that the second metric data does not satisfy either the first threshold or the second threshold, exclude the dark-field image data from use in determining the position data.

8. The computer system of claim 7, wherein the instructions for obtaining the projection image data cause the processor to:

obtain the projection image data that is generated using a grating-based imaging system that includes the imaging source, the detector and multiple gratings that are positioned between the imaging source and the detector.

9. The computer system of claim 8, wherein the instructions for generating (a) the phase-contrast image data and (b) the dark-field image data cause the processor to:

determine first parameter data associated with the projection image data that includes a set of multiple projection images associated with a set of respective multiple phase steps, wherein the first parameter data includes first intensity offset data, first amplitude data and first phase data;

determine second parameter data associated with reference image data that is generated using the grating-based imaging system without the patient, wherein the reference image data includes a set of multiple reference images associated with the set of respective multiple phase steps, wherein the second parameter data includes second intensity offset data, second amplitude data and second phase data; and based on the first parameter data and the second parameter data, generate (a) the phase-contrast image data, (b) the dark-field image data and (c) absorption image data.

10. The computer system of claim 7, wherein the instructions further cause the processor to:

generate the derived image data by applying one or more function to combine or calculate a ratio between at least two of the following: (a) the phase-contrast image data, (b) the dark-field image data and (c) absorption image data.

11. The computer system of claim 7, wherein the instructions for determining the 2D or 3D position data cause the processor to:

based on a motion model associated with the target structure, generate three-dimensional (3D) volume image data associated with at least one of the following two-dimensional (2D) projection image data: (a) the phase-contrast image data, (b) the dark-field image data and (c) the derived image data; and determine 3D position data associated with the target structure based on (a) reference 3D volume image data acquired prior to the treatment phase and (b) the generated 3D volume image data.

12. The computer system of claim 7, wherein the instructions for determining the position data cause the processor to:

determine 2D or 3D position data associated with the target structure using an artificial intelligence (AI) engine to process at least one of the following: (a) the phase-contrast image data, (b) the dark-field image data and (c) the derived image data, wherein the AI engine includes multiple processing layers that are trained to perform position data estimation.

13. A radiation therapy system, comprising:

a grating-based imaging system that includes an imaging source, a detector and multiple gratings that are positioned between the imaging source and the detector; and a computer system to perform the following:

obtain, from the grating-based imaging system, projection image data that is generated using the imaging source to emit an imaging beam towards the multiple gratings and the detector to image a target structure within the patient during a treatment phase of radiation therapy;

based on the projection image data, generate at least one of (a) phase-contrast image data associated with the target structure and (b) dark-field image data associated with the target structure; and determine two-dimensional (2D) or three-dimensional (3D) position data associated with the target structure by processing at least one of the following: (a) the phase-contrast image data, (b) the dark-field image data and (c) derived image data that is generated based on the phase-contrast image data or the dark-field image data, thereby tracking the target structure during the treatment phase of the radiation therapy, wherein the computer system is to determine the 2D or 3D position data associated with the target structure by performing:

determining first metric data associated with the phase-contrast image data and second metric data associated with the dark-field image data;

in response to determination that the first metric data satisfies a first threshold, selecting the phase-contrast image data for use in determining the 2D or 3D position data; and in response to determination that the first metric data does not satisfy the first threshold, excluding the phase-contrast image data from use in determining the 2D or 3D position data; and in response to determination that the second metric data satisfies the first threshold or a second threshold, selecting the dark-field image data for use in determining the 2D or 3D position data; and in response to determination that the second metric data does not satisfy either the first threshold or the second threshold, excluding the dark-field image data from use in determining the 2D or 3D position data.

14. The radiation therapy system of claim 13, wherein the computer system is to generate (a) the phase-contrast image data and (b) the dark-field image data by performing the following:

determine first parameter data associated with the projection image data that includes a set of multiple projection images associated with a set of respective multiple phase steps, wherein the computer system is to the first parameter data includes first intensity offset data, first amplitude data and first phase data;

determine second parameter data associated with reference image data that is generated using the grating-based imaging system without the patient, wherein the computer system is to the reference image data includes a set of multiple reference images associated with the set of respective multiple phase steps, wherein the computer system is to the second parameter data includes second intensity offset data, second amplitude data and second phase data; and based on the first parameter data and the second parameter data, generate (a) the phase-contrast image data, (b) the dark-field image data and (c) absorption image data.

15. The radiation therapy system of claim 13, wherein the computer system is further to perform the following:

generate the derived image data by applying a function to combine or calculate a ratio between at least two of the following: (a) the phase-contrast image data, (b) the dark-field image data and (c) absorption image data.

16. The radiation therapy system of claim 13, wherein the computer system is to determine the 2D or 3D position data by performing the following:

based on a motion model associated with the target structure, generate three-dimensional (3D) volume image data associated with at least one of the following two-dimensional (2D) projection image data: (a) the phase-contrast image data, (b) the dark-field image data and (c) the derived image data; and determine 3D position data associated with the target structure based on (a) reference 3D volume image data acquired prior to the treatment phase and (b) the generated 3D volume image data.

17. The radiation therapy system of claim 13, wherein the computer system is to determine the position data by performing the following:

determine the 2D or 3D position data associated with the target structure using an artificial intelligence (AI) engine to process at least one of the following: (a) the phase-contrast image data, (b) the dark-field image data and (c) the derived image data, wherein the computer system is to the AI engine includes multiple processing layers that are trained to perform position data estimation.

* * * * *